United States Patent [19]

Nishiyama et al.

[11] 4,406,841
[45] Sep. 27, 1983

[54] PROCESS FOR PRODUCING 2,6-DIFLUOROBENZONITRILE

[75] Inventors: Ryuzo Nishiyama, Takatsuki; Kanichi Fujikawa; Yasuhiro Tsujii, both of Moriyama; Shigeo Murai, Yohkaichi; Hisayoshi Jyonishi, Shiga, all of Japan

[73] Assignee: Ishihara Sangyo Kaisha Ltd., Osaka, Japan

[21] Appl. No.: 408,932

[22] Filed: Aug. 17, 1982

[30] Foreign Application Priority Data

Aug. 31, 1981 [JP] Japan ................................. 56-136659
Apr. 30, 1982 [JP] Japan ................................. 57-72630

[51] Int. Cl.$^3$ .......................................... C07C 121/52
[52] U.S. Cl. ................................................ 260/465 G
[58] Field of Search ..................................... 260/465 G

[56] References Cited

U.S. PATENT DOCUMENTS 3,290,353 12/1966 Battershell et al. ............ 260/465 G
4,209,457 6/1980 Fuller ............................. 260/465 G Primary Examiner—Dolph H. Torrence
Attorney, Agent, or Firm—Oblon, Fisher, Spivak, McClelland & Maier

[57] ABSTRACT

A process for producing 2,6-difluorobenzonitrile comprises reducing a chloro fluorobenzonitrile selected from 3-chloro-2,6-difluorobenzonitrile, 3,5-dichloro-2,6-difluorobenzonitrile or a mixture thereof by hydrogen gas in the presence of a palladium or platinum catalyst at a temperature of 0° to 200° C.

11 Claims, No Drawings

PROCESS FOR PRODUCING 2,6-DIFLUOROBENZONITRILE

BACKGROUND OF THE INVENTION

1. Field of the Invention

The present invention relates to a novel and industrially advantageous process for producing a 2,6-difluorobenzonitrile (hereinafter referred to as DFBN) useful as raw material of medicines and agricultural chemicals.

2. Description of the Prior Art

Heretofore, a process for producing the DFBN has been known, for example, by the Journal of Agricultural Food Chemistry vol. 21, No. 6, page 933 (1973), Shinjikken kagakukoza vol. 14, No. 1, page 322 (1977), wherein the DFBN is prepared by reacting 2,6-dichlorobenzonitrile (hereinafter referred to as DCBN) with potassium fluoride in the presence of a solvent such as dimethylsulfoxide and sulforane at a temperature higher than 180° C. for at least several hours. However, this process has many disadvantages. For example, (i) the DCBN raw material is hardly available in an economically feasible way, (ii) it is required to use the potassium fluoride considerably in excess of the stoichiometric amount required for said fluorination, for example at a molar ratio of more than twice the stoichiometric amount, and (iii) the yield of the desired DFBN is low. When severe reaction conditions are used to improve te yield, undesirable side reactions and decomposition of the solvent are likely to take place.

SUMMARY OF THE INVENTION

The present inventors have studied the process for producing the DFBN and found the following:

(i) It is extremely difficult to obtain the DCBN industrially from p-toluenesulfonic acid. On the other hand, a chlorobenzonitrile (hereinafter referred to as CBN) such as 2,3,6-trichlorobenzonitrile or 2,3,5,6-tetrachlorobenzonitrile can be derived from said p-toluenesulfonic acid quite easily, and can advantageously be used as raw material.

(ii) When the CBN is fluorinated by potassium fluoride in the presence of a special solvent, a chloro fluorobenzonitrile (hereinafter referred to as CFBN) such as 3-chloro-2,6-difluorobenzonitrile or 3,5-dichloro-2,6-difluorobenzonitrile is obtainable.

(iii) When the CFBN is reduced by hydrogen gas in the presence of a special catalyst, the desired DFBN is obtained in good yield.

In particular, the present invention is based on the following findings.

(1) It has been unexpectedly found that in the fluorination of CBN according to the present invention, a smaller amount of potassium fluoride is required, the reaction proceeds under milder conditions, the formation of by-products is less and the yield of the fluorination product is according better than in the fluorination of DCBN according to the conventional process.

(2) At the initial stage of the study on a relation between the chemical structure of the CFBN and its reductive property, the present inventors could not anticipate which one of the fluorine atom and chlorine atom in the benzene ring of CFBN would be reduced and dehalogenated, because it would be considered from the general common knowledge in the organic synthesis that the fluorine atom would be bonded more strongly to the ring than the chlorine atom, while the fluorine atom would be reduced more easily than the chlorine atom since the fluorine atom is present in the ortho position to the electron attractive cyano group and the chlorine atom is present in the metha position thereto.

(3) In addition, it was considered possible that both of the fluorine and chlorine atoms would be reduced, or the cyano group would also be reduced depending upon the nature of the reduction or the conditions thereof. According to the present invention, a special catalyst and solvent are used whereby only the chlorine atom is selectively reduced by the catalytic reduction without accompanying the reduction of the fluorine atom and cyano group, and the desired DFBN can thereby be obtained in good yield.

The present invention provides a process for producing 2,6-difluorobenzonitrile which comprises reducing a chloro fluorobenzonitrile selected from 3-chloro-2,6-difluorobenzonitrile, 3,5-dichloro-2,6-difluorobenzonitrile and a mixture thereof by hydrogen gas in the presence of a palladium or platinum catalyst at a temperature of 0° to 200° C., or fluorinating a chlorobenzonitrile selected from 2,3,6-trichlorobenzonitrile, 2,3,5,6-tetrachlorobenzonitrile and a mixture thereof by potassium fluoride in the presence of an aprotic polar solvent at a temperature of 100° to 250° C. to form said chloro fluorobenzonitrile, which is followed by the above mentioned catalytic reduction.

According to the present invention, there can be obtained the following advantages for example;

(1) The CBN raw material can readily be prepared industrially from an inexpensive material by usual reactions: Namely, the CBN can readily be prepared by chlorinating p-toluenesulfonic acid which is economically advantageously available, then desulfonating the chlorination product to form trichloro or tetrachlorotoluene, and ammoxidating the chlorotoluene.

(2) Both steps of the fluorination and reduction can be carried out under mild reaction conditions such as the reaction time and reaction temperature and a side reaction hardly occurs, whereby the desired DFBN can be obtained in good yield. The yield of DFBN through both steps is higher than the yield attainable by the conventional fluorination of DCBN.

(3) In the present invention, the amount of the potassium fluoride required as a raw material for the fluorination reaction is almost a stoichiometric amount and it is thereby possible to substantially save the potassium fluoride as compared with the conventional process.

(4) In both reaction steps, the solvent, catalyst and acceptor of hydrochloric acid can readily be recovered by a simple method, and they can advantageously be reused.

(5) The synthetic route of the process of the present invention is longer than that of the conventional process comprising the fluorination of DCBN. However, the process of the present invention provides, in addition to the above mentioned advantages in the fluorination of DCBN, a substantially improved yield of DFBN with use of a readily available inexpensive raw material. Thus, the process of the present invention is industrially superior to the conventional process.

DETAILED DESCRIPTION OF THE PREFERRED EMBODIMENTS

The CBN used as raw material in the process of the present invention can be produced, for example, by the following method. Chlorine gas is introduced into p-methylbenzenesulfonic acid in the presence of concentrated sulfuric acid and iodine at a temperature of 50° to 150° C., whereby 2,3,5-trichloro or 2,3,5,6-tetrachloro-4-methylbenzenesulfonic acid can readily be obtained. After an addition of water, it is heated and desulfurized by passing a steam at an elevated temperature, whereby 2,3,6-trichloro or 2,3,5,6-tetrachlorotoluene is obtained. Then, the chlorotoluene is reacted with air and ammonia gas in the presence of a vanadium-ion catalyst, if necessary in the presence of nitrogen gas as a carrier, at a temperature of 300° to 600° C. in a gaseous phase to form the CBN. This reaction is called an ammoxidation reaction.

In an industrial process using these reactions, CBN is obtainable usually as a mixture of 2,3,6-trichlorobenzonitrile and 2,3,5,6-tetrachlorobenzonitrile. In the process of the present invention, this mixture can be used as it is, as raw material for the next fluorination step.

Fluorination Step:

According to the present invention, the CBN and potassium fluoride are usually added to an aprotic polar solvent and reacted under heating to obtain the CFBN. The aprotic polar solvent can be an amide solvent, dimethylsulfoxide, dimethylsulfone, sulforane and the like. Particularly preferred for an industrial operation is an amide solvent which is inert to the fluorination reaction. For instance, there may be mentioned dimethyl acetoamide, dimethyl formamide, N-methyl-2-pyrrolidone, N-cyclohexyl-2-pyrrolidone and 1,3-dimethyl-2-imidazolidinone. When a substance containing a sulfur atom in its structure is used as the solvent, a due care has to be taken into accounts the possibility that even a small amount of such a solvent or a by-product having the sulfur atom, if left in the fluorination product, will adversely affect the catalyst used in the subsequent catalytic reaction step whereby the activity of the catalyst will be reduced or impaired.

The amount of the solvent is not critical and depends on the CBN, solvent, reaction conditions and the like. In general, however, it is 2 to 30 times, preferably 3 to 10 times, by weight, the amount of the CBN. The potassium fluoride to be used, may be a commercially available material or finely pulverized particles. The amount of the potassium fluoride is also not critical and is generally 1 to 2 times, preferably 1 to 1.5 times the stoichiometric amount required for substituting two chlorine atoms in the 2 and 6 positions of the CBN with two fluorine atoms. In general, the reaction temperature is in a range of 100° to 250° C. preferably 120° to 180° C. and the reaction time is in a range of 1 to 10 hours.

The fluorination product is subjected to a usual separation operation including filtration, liquid phase separation, distillation and the like whereupon the CFBN or its mixture can be obtained in good yield. Further, when the liquid phase separation is carried out with an addition of water to the fluorination product, the solvent can readily be recovered from the aqueous phase.

Reduction Step:

The CFBN obtained in the former step is reduced by hydrogen gas in the presence of a palladium or platinum catalyst to form the desired DFBN. The catalyst can be a palladium or platinum catalyst which is commonly used for catalytic reduction, such as palladium or platinum oxide. Preferred is palladium. The reduction may be carried out in the presence of a solvent or an acceptor of hydrochloric acid. The solvent can be water or an alcohol such as methanol or ethanol. Water is preferred for industrial purposes. The acceptor of hydrochloric acid can be a tertiary amine, or a hydride of an alkaline metal or alkaline earth metal, a hydroxide or carbonate thereof. The tertiary amine is preferred.

The palladium or platinum catalyst may be used as it is. However, it is usually mixed with a carrier such as active carbon, coke, alumina, diatomaceous earth or silicagel and formulated into granules or pellets with an appropriate size for practical use. The amount of the catalyst is not critical, but in general, it is used in a range of 0.01 to 10 g, preferably 0.05 to 0.5 g as the catalytically active ingredient based on 1000 g of the CFBN. It is industrially advantageous to perform a reaction by putting the catalyst on the fixed bed. Any tertiary amine can be used, so long as it serves as an acceptor of hydrochloric acid. As specific examples, there may be mentioned triethylamine, trimethylamine and pyridine. The tertiary amine is used usually in an amount of 1 to 10 moles, preferably 1 to 2 moles based on one mole of the CFBN.

Usually, the reduction is carried out in an autoclave while the pressure of hydrogen gas in the reaction system is kept in a range of 5 to 50 kg/cm$^2$. The reaction temperature is in a range of 0° C. to 200° C., preferably 50° to 100° C. and a reaction time is in a range of 1 to 10 hours.

The reduction product is subjected to a usual separation operation including filtration, liquid phase separation, distillation and the like, whereupon the DFBN can be obtained in good yield. By the filtration of the reduction product the catalyst can be recovered. Likewise, the tertiary amine can readily be recovered from the aqueous phase by adjusting the pH of the aqueous phase.

Further, 3-chloro-2,6-difluorobenzonitrile i.e. an intermediate product obtained in the process of the present invention, is a novel compound and can be chemically converted into a compound having a high physiological activity. Thus, it has been confirmed that this compound is useful as an intermediate for the preparation of a compound effective as an agricultural chemical compound or medicine.

For example, when 3-chloro-2,6-difluorobenzonitrile is dissolved in methanol and reacted with hydrogen gas in the presence of palladium-carbon catalyst and triethylamine under the hydrogen pressure of 5 kg/cm$^2$, the DFBN is obtainable. The DFBN is then heated and dissolved at 70° C. and dropwise added to 90% sulfuric acid, and the reaction is performed at 70° to 80° C. to obtain a 2,6-difluorobenzamide. The product is then dissolved in 1,2-dichloroethane and an oxyalyl chloride is dropwise added to the solution at 20° to 40° C., and the reaction is performed under reflux to obtain 2,6-difluorobenzoyl isocyanate. A dioxane solution of 3,5-dichloro-4-(3-chloro-5-trifluoromethyl-2-pyridyloxy) aniline is dropwise added to a dioxane solution of the isocyanate at 40° to 50° C. and the reaction was performed to obtain N-(2,6-difluorobenzoyl)-N'-[3,5-dichloro-4-(3-chloro-5-trifluoromethyl-2-pyridyloxy)-phenyl]urea having a melting point of 203° to 205° C. This derivative is effective to combat a various kinds of undesirable insects, as disclosed in the Japanese Unexamined Patent Publication 125677/1979, U.S. Pat. Nos. 4,173,637, 4,173,638 and 4,310,530.

The present invention will be further illustrated by certain examples and references which are provided for purpose of illustration only and are not intended to be limiting the present invention.

EXAMPLE 1

(1) Fluorination Step:

In 100 g of N-methyl-2-pyrrolidone, 20.6 g of 2,3,6-trichlorobenzonitrile was dissolved and 13.9 g of potassium fluoride was added to the solution. The reaction was carried out at 190° C. for 4 hours with stirring. The reaction mixture was filtered to separate potassium fluoride and potassium chloride from it, and water was added to the filtrate to perform liquid phase separation. The oil phase was distilled to obtain 16.5 g of 3-chloro-2,6-difluorobenzonitrile having a boiling point of 95° C./11 mmHg (yield: 95%). The aqueous phase was distilled to recover 98 g of N-methyl-2-pyrrolidone (recovery rate: 98%).

(2) Reduction Step:

To 80 ml of water, 17 g of 3-chloro-2,6-difluorobenzonitrile obtained in the above step, was added and 0.085 g of palladium-carbon catalyst (element ratio by weight: Pd:C=2:100) and 12 g of triethylamine were further added to it. The reaction was carried out in an autoclave at 100° C. for 3 hours while introducing hydrogen gas into it so that the pressure of hydrogen gas in the reaction system was kept at 10 kg/cm$^2$. The catalyst was filtered, and a small amount of dilute hydrochloric acid was added to the filtrate to adjust a value of pH at 5. The oil phase was separated by liquid phase separation and distilled to obtain 13.6 g of 2,6-difluorobenzonitrile (yield: 98%). The aqueous phase was made basic by an addition of a small amount of an aqueous solution of sodium hydroxide, whereupon 11 g of triethylamine (recovery ratio: 91%) was recovered.

EXAMPLES 2 and 3

(1) Fluorination Step:

In a predetermined amount of a solvent, a mixture of 171 g of 2,3,6-trichlorobenzonitrile and 16 g of 2,3,5,6-tetrachlorobenzonitrile was dissolved and a predetermined amount of potassium fluoride was added to the solution. The reaction was carried out with stirring. Then, in the same manner as in the process of Example 1, the CFBN and solvent were recovered. The results thereby obtained are shown in the following Table 1.

TABLE 1

| No. | 2 | 3 |
|---|---|---|
| Amount of solvent (g) | NMP 900 | NMP 800 |
| Amount of KF (g) | 156 | 124 |
| Reaction condition | | |
| Temperature (°C.) | 190 | 190 |
| Time (hrs.) | 2.5 | 3.5 |
| CFBN | | |
| Amount of 3-Cl—2,6-F$_2$ type (g) | 143.7 | 135.0 |
| Amount of 3,5-Cl$_2$—2,6-F$_2$ type (g) | 8.0 | 6.6 |
| Yield (%) | 93.7 | 90.6 |
| Recovery amount of solvent (g) | 864 | 736 |

Note:
(1) NMP; N—methyl-2-pyrrolidone
(2) 3-Cl—2,6-F$_2$ type; 3-chloro-2,6-difluorobenzonitrile
(3) 3,5-Cl$_2$—2,6-F$_2$ type; 3,5-dichloro-2,6-difluorobenzonitrile (2) Reduction Step:

To the fluorination product obtained in the above step, 450 ml of water was added, and a predetermined amount of palladium-carbon catalyst (element ratio by weight: Pd:C=2:100) and triethylamine as an acceptor of hydrochloric acid were added to it. Then, in the same manner as in the process of Example 1, the DFBN and triethylamine were recovered. The results thereby obtained are shown in the following Table 2.

TABLE 2

| No. | 2 | 3 |
|---|---|---|
| Amount of catalyst (g) | 7.5 | 1.5 |
| Amount of HCl acceptor (g) | 110 | 100 |
| Reaction condition | | |
| Temperature (°C.) | 120 | 120 |
| Time (hrs.) | 3 | 4 |
| Hydrogen pressure (kg/cm$^2$) | 10 | 10 |
| DFBN | | |
| Amount (g) | 120 | 107.9 |
| Yield (%) | 99 | 96 |
| Recovery amount of HCl acceptor (g) | 108 | 98 |

EXAMPLE 4

(1) Chlorination and Desulfonation Steps:

To a solution of 130 g of one hydrate of p-toluenesulfonic acid and 767 g of sulfuric acid, 1.3 g of potassium iodide was added and chlorine gas was fed into it at a rate of 0.12 Nl per minute at 80° to 90° C. to perform the reaction for 8 hours. The reaction product and 190 ml of water were heated, and a superheated steam was introduced into them, whereby a desulfonation reaction was carried out and at the same time, the reaction product was distilled as an azeotropic mixture with water to obtain 137 g of a distillate (yield: 80%). The distillate was rectified to obtain an oil composed of 8.9% of 2,3,6-trichlorobenzonitrile, 90.1% of 2,3,5,6-tetrachlorobenzonitrile and 1.0% of others.

(2) Ammoxidation Step:

In an electric furnace, γ-alumina was heated at 1100° C. for 2 hours. A suspension of 17.8 g of vanadium pentoxide and 110 ml of water was heated and kept at 80° to 90° C. To the suspension, 63 g of two hydrates of oxalic acid was added to prepare a solution of vanadyl oxalate. The solution of vanadyl oxalate was mixed with a solution of 400 g of nona-hydrate of ferric nitrate and 210 ml of water, and this mixture was added to 1000 g of the alumina, so that the alumina was fully impregnated with the mixture. The impregnated alumina was dried and calcined in an air stream at 450° C. for 2 hours to obtain an oxide. To the catalyst packing zone of a fluidized-bed reactor, 2.2 kg of the oxide was charged and heated.

An oil of chlorotoluene composed of 2.5% of 2,3,6-trichlorotoluene and 94.6% of 2,3,5,6-tetrachlorotoluene was vaporized at a rate of 1.37 g per minute, and it was mixed with preheated ammonia gas, air and nitrogen gas at a rate of 0.27 Nl, 1.33 Nl and 0.67 Nl per minute, respectively, and the mixture was introduced into the reactor. The reaction was carried out under a fluidizing condition at 350° C. for 6 hours and 40 minutes, and the residence time of the reaction mixture in the reaction zone was about 25 seconds.

The gaseous product was introduced to a cooler and a receiver to obtain a crystallized product composed of 2.4% of 2,3,6-trichlorobenzonitrile, 84.7% of 2,3,5,6- tetrachlorobenzonitrile and 12.9% of others, and it was rectified to obtain 392 g of the product (yield: 79.5%).

(3) Fluorination Step:

In 100 g of N-methyl-2-pyrrolidone, 20 g of 2,3,5,6-tetrachlorobenzonitrile was dissolved and 11.6 g of potassium fluoride was added at the solution. The reaction was carried out at 160° C. for 2 hours. In the same manner as in the process of the fluorination step of Example 1, the reaction mixture was refined to obtain 16.8 g of 3,5-dichloro-2,6-difluorobenzonitrile having a boiling point of 100° C./10 mmHg (yield: 97.6%) and 89.7 g of N-methyl-2-pyrrolidone was recovered (recovery rate: 89.7%).

(4) Reduction Step:

To 45 ml of water 15 g of 3,5-dichloro-2,6-difluorobenzonitrile was added and 0.05 g of palladium-carbon catalyst and 17.5 g of triethylamine were added to it. The reaction was carried out in an autoclave at 120° C. for 7 hours while introducing hydrogen gas into it so that the pressure of hydrogen gas in the reaction system was kept at 30 kg/cm$^2$. In the same manner as in the process of the reduction step of Example 1, the reaction mixture was refined to obtain 9.6 g of 2,6-difluorobenzonitrile (yield: 95.8%) and 15.6 g of triethylamine was recovered (recovery rate: 89.1%).

EXAMPLE 5

(1) Ammoxidation Step:

A fluidized catalytic bed-type gaseous phase reactor equipped with an air-cooling type receiver at the outlet of a reaction tube and having two tubes for supplying raw materials, was used. A catalyst comprising ferric oxide and vanadium pentoxide supported an alumina of 48 to 100 mesh and having an element ratio by weight of Al:Fe:V=100:5:1, was charged into the reactor. Through one of the supplying tubes, a gas (molar ratio: 2,3,6-trichlorotoluene:benzonitrile:nitrogen=0.5:0.5:5) which was produced by vaporizing a solution of the toluene in benzonitrile and diluting the vapor with nitrogen gas, was fed so that the toluene was supplied at a rate of 19.5 g per hour. Through the other supplying tube, a mixed gas of ammonia and air (molar ratio: ammonia:air=10:16) was fed so that the ammonia was supplied at a rate of 36 g per hour. The reaction was carried out at 360° C. for 10 hours and the residence time of the reaction mixture in the reaction tube was 25 seconds.

The reaction product in the receiver was extracted with methylene chloride and the extract was washed with water and concentrated. The concentrate was recrystallized from n-hexane to obtain 85 g of 2,3,6-trichlorobenzonitrile having a melting point of 117°–119° C.

(2) Fluorination Step:

In 800 g of dimethylsulfoxide, 206.5 g of 2,3,6-trichlorobenzonitrile obtained in the above step was dissolved and 145.3 g of potassium fluoxide was added to the solution. The reaction was carried out at 170° C. for 1.5 hours with stirring. Then, the reaction mixture was poured into water and extracted with methylene chloride. After the solvent was distilled off, the mixture was distilled to obtain 166.6 g of 3-chloro-2,6-difluorobenzonitrile having a boiling point of 95° C./11 mmHg (yield: 96.0%).

(3) Reduction Step:

In the same manner as in the process of the reduction step of Example 1, the reaction was carried out at 40° C. for 2.5 hours by using 10 g of 3-chloro-2,6-difluorobenzonitrile, 60 g of water, 0.25 g of palladium-carbon catalyst and 3 g of sodium hydroxide, and refinement was carried out to obtain 5.63 g of 2,6-difluorobenzonitrile.

COMPARATIVE TEST 1

In the same manner as in the process of the fluorination step of Example 1 except for using 17.2 g of 2,6-dichlorobenzonitrile instead of 2,3,6-trichlorobenzonitrile, the reaction and refinement were carried out to obtain 9.5 g of 2,6-difluorobenzonitrile (yield: 68%).

COMPARATIVE TEST 2

In 280 g of dimethylsulfoxide, 80 g of 2,6-dichlorobenzonitrile was dissolved and 109 g of potassium fluoride was added to the solution. The reaction was carried out at 189° C. for 3 hours. Then, in the same manner as in the process of the fluorination step of Example 1, a reaction product was refined to obtain 43 g of 2,6-difluorobenzonitrile (yield: 67%). The reaction product contained about 5.4% by weight of a by-product.

COMPARATIVE TEST 3

An experiment was carried out in the same manner as in the fluorination step of Example 1 by changing the palladium-carbon catalyst to the Raney nickel.

To 50 ml of water, 10 g of a mixture comprising 7.8% of 2,3,6-trichlorotoluene, 87.2% of 3-chloro-2,6-difluorobenzonitrile and 2.7% of 3,5-dichloro-2,6-difluorobenzonitrile was added and one g of the Raney nickel-carbon catalyst (element ratio by weight: Ni:C=1:100) and 10 g of triethylamine were added to it. The reaction was carried out in an autoclave at 100° C. for 9 hours while introducing hydrogen gas to it so that the pressure of hydrogen gas in the reaction system was kept at 10 kg/cm$^2$. In the same manner as in the process of the fluorination step of Example 1, the reaction mixture was refined to obtain an oil phase. The composition of the oil phase was analyzed and it was found that the objective 2,6-difluorobenzonitrile was not contained substantially, but a by-product was contained in a large amount.

We claim:

1. A process for producing 2,6-difluorobenzonitrile which comprises reducing a chloro fluorobenzonitrile selected from 3-chloro-2,6-difluorobenzonitrile, 3,5-dichlor-2,6-difluorobenzonitrile or a mixture thereof by hydrogen gas in the presence of a palladium or platinum catalyst at a temperature of 0° to 200° C.

2. The process according to claim 1 wherein the catalyst is palladium.

3. The process according to claim 1 wherein the catalytic reduction is carried out under the pressure of hydrogen gas of 5 to 50 kg/cm$^2$.

4. The process according to claim 1 wherein the catalytic reduction is carried out in the presence of 1 to 10 mole of a tertiary amine compound based on one mole of the chloro fluorobenzonitrile.

5. The process according to claim 1 wherein the catalytic reduction is carried out in the presence of 0.01 to 10 g of the catalyst as the catalytically active ingredient based on 1000 g of the chloro fluorobenzonitrile.

6. The process according to claim 1 wherein catalytic reduction is carried out at a temperature of 50° to 150° C.

7. A process for producing 2,6-difluorobenzonitrile which comprises fluorinating a chlorobenzonitrile selected from 2,3,6-trichlorobenzonitrile, 2,3,5,6-tetrachlorobenzonitrile or a mixture thereof by potassium fluoride in the presence of an aprotic polar solvent at a temperature of 100° to 250° C. to form a chloro fluorobenzonitrile selected from 3-chloro-2,6-difluorobenzonitrile, 3,5-dichloro-2,6-difluorobenzonitrile or a mixture thereof and reducing the chloro fluorobenzonitrile by hydrogen gas in the presence of a palladium or platinum catalyst at a temperature of 0° to 200° C.

8. The process according to claim 7 wherein the fluorination is carried out in the presence of an amide compound as the solvent and the catalytic reduction is carried out in the presence of palladium as the catalyst under the pressure of hydrogen gas of 5 to 50 kg/cm$^2$.

9. The process according to claim 7 wherein the fluorination is carried out by using the potassium fluoride in an amount of 1 to 2 times the stoichiometric amount required for substituting two chlorine atoms at the 2 and 6 positions of the chlorobenzonitrile with two fluorine atoms and the catalytic reduction is carried out in the presence of 1 to 10 mole of a tertiary amine compound based on one mole of the chloro fluorobenzonitrile and in the presence of 0.01 to 10 g of the catalyst as the catalytically active ingredient based on 1000 g of the chloro fluorobenzonitrile.

10. The process according to claim 7 wherein the fluorination is carried out at a temperature of 120° to 180° C. and the catalytic reduction is carried out at a temperature of 50° to 150° C.

11. 3-Chloro-2,6-difluorobenzonitrile.

* * * * *